United States Patent [19]

Newell

[11] 4,220,168

[45] Sep. 2, 1980

[54] METHOD OF MOISTURIZING AND MAINTAINING NORMAL MOISTURE LEVEL IN HAIR HAVING A NORMAL MOISTURE CONTENT

[75] Inventor: Gerald P. Newell, Hanover Park, Ill.

[73] Assignee: Helene Curtis Industries, Inc., Chicago, Ill.

[21] Appl. No.: 912,362

[22] Filed: Jun. 5, 1978

[51] Int. Cl.² .................... A45D 7/04; A61K 7/06
[52] U.S. Cl. ........................... 132/7; 424/70; 424/71
[58] Field of Search ............... 132/7, 9; 424/70, 71, 424/65, DIG. 2, 362, 365

[56] References Cited

U.S. PATENT DOCUMENTS

| | | | |
|---|---|---|---|
| 3,235,457 | 2/1966 | Laden | 424/70 X |
| 3,450,674 | 6/1969 | Walles | 424/71 |
| 3,683,939 | 8/1972 | Johnson | 424/70 |
| 3,822,312 | 7/1974 | Sato et al. | 424/70 |
| 3,948,943 | 4/1976 | Eberhardt et al. | 424/65 |
| 4,047,537 | 9/1977 | Shaw | 132/7 |
| 4,076,800 | 2/1978 | Marsh et al. | 424/70 |
| 4,115,549 | 9/1978 | Scott | 132/7 X |

FOREIGN PATENT DOCUMENTS

| | | | |
|---|---|---|---|
| 44-22440 | 9/1969 | Japan . | |
| 49-27643 | 7/1974 | Japan | 424/70 |
| 51-20639 | 6/1976 | Japan | 424/70 |
| 7604794 | 11/1976 | Netherlands | 424/70 |

OTHER PUBLICATIONS

Drug & Cosmetic Industry 84 (4) at p. 440t, (1960) Thomsen.
Cosmetics Science and Technology–Editor Edward Sagarin, Interscience Publishers, Inc., New York, 1957, pp. 382–383, 405.
American Perfumer and Cosmetics–vol. 78, No. 10, Oct. 1963, Proteins in Cosmetics, pp. 69–72.

*Primary Examiner*—Stuart S. Levy
*Attorney, Agent, or Firm*—Dressler, Goldsmith, Shore, Sutker & Milnamow, Ltd.

[57] ABSTRACT

A method of moisturizing and maintaining the normal moisture level in hair initially having a normal moisture content comprising the steps of: (1) shampooing the hair with a moisture stabilizing shampoo; (2) conditioning the hair with a moisture stabilizing conditioner; and (3) thereafter applying a moisture control styling lotion, said shampoo, conditioner and styling lotion each containing from 0.01 to 1.0 weight percent of 2-pyrrolidone-5-carboxylic acid or a salt thereof, from 0.01 to 5.0 weight percent glycerin and from 0.01 to 5.0 weight percent of protein derived from a collagenous source.

5 Claims, No Drawings

METHOD OF MOISTURIZING AND MAINTAINING NORMAL MOISTURE LEVEL IN HAIR HAVING A NORMAL MOISTURE CONTENT

BACKGROUND OF THE INVENTION

This invention relates to a method for maintaining a normal moisture level in hair initially having a normal moisture content.

The use of hair coloring or bleaching products, permanents, straighteners, blowdryers and exposure to sun, wind, indoor heating, etc. are all drying and damage the hair by robbing it of moisture. Moisture deficient hair is dull, brittle and lifeless.

A number of products have been developed in recent years to improve the condition of hair. While many of the available hair-conditioning compositions improve the sheen, combability and manageability of hair, they do little to restore and maintain the normal moisture content of hair. Thus there is a need for improved products and methods which can restore and maintain the normal moisture content of hair as well as condition it to improve its sheen, combability and the like. The present invention provides a method for achieving this result.

Laden U.S. Pat. No. 3,235,457, issued Feb. 15, 1966, discloses the use of the free acid or the hygroscopic salts of 2-pyrrolidone-5-carboxylic acid, 1-methyl-2-pyrrolidone-5-carboxylic acid and 4-methyl-2-pyrrolidone-5-carboxylic acid as humectants in cosmetic compositions which are to be applied to hair or skin. Laden discloses incorporating the humectants into the cosmetics and other compositions to prevent the products from losing moisture and drying out in storage. Laden further teaches that the humectants must be present in an amount of at least 2 weight percent of such compositions, and preferably from 4 to 10 weight percent. Glycerin is also known to be a humectant.

It has now surprisingly been found that when from about 0.01 to about 1 weight percent of sodium-2-pyrrolidone-5-carboxylate is incorporated into hair treatment compositions such as shampoos, conditioners, and the like, along with glycerin and protein derived from a collagenous source, and such compositions are used in concert with each other in a prescribed manner, the moisture level can be advantageously maintained in hair initially having a normal moisture content.

Thus the present invention provides an improved process for maintaining the normal moisture level in hair initially having a normal moisture content.

SUMMARY OF THE INVENTION

A method of moisturizing and maintaining the normal moisture level in hair initially having a normal moisture content comprising the steps of: (1) shampooing the hair with a moisture stabilizing shampoo; (2) conditioning the shampooed hair with a moisture stabilizing conditioner; and (3) thereafter applying a moisture control styling lotion, said shampoo, conditioner and styling lotion each containing from about 0.01 to about 1.0 weight percent of 2-pyrrolidone-5-carboxylic acid or a salt thereof, from about 0.01 to about 5.0 weight percent of glycerin, and from about 0.01 to about 5.0 weight percent of protein derived from a collagenous source. Hereinafter, the unique combination of the three ingredients will be referred to as the two humectants and protein.

The term "moisture stabilizing shampoo" refers to a shampoo containing the above two humectants and protein.

The term "moisture stabilizing conditioner" refers to a conditioner containing the combination of two humectants and protein which is applied to the hair after shampooing and then immediately rinsed from the hair.

The term "moisture control styling composition" refers to styling compositions which are applied prior to the hair being set, or if the hair is to be blown dry, to blow dry compositions as set forth hereinbelow, both of which contain the two humectants and protein.

In addition to the unique combination of the sodium-2-pyrrolidone-5-carboxylate, glycerin and protein in the compositions which are used in the practice of this invention, the compositions may additionally comprise quaternary conditioners, detergents, thickeners, fatty esters, non-quaternary conditioning agents, fragrance, fragrance solubilizers and the like as is common in such compositions.

DETAILED DESCRIPTION OF THE PREFERRED EMBODIMENTS

The present invention provides a method of maintaining the normal moisture level of hair comprising the steps of: (1) shampooing the hair with a moisture stabilizing shampoo; (2) conditioning the shampooed hair following each shampoo with a moisture stabilizing conditioner; and (3) styling the shampooed, conditioned hair with a moisture control styling composition, each of said shampoos, styling lotions and conditioners comprising from about 0.01 to about 1 weight percent of sodium-2-pyrrolidone-5-carboxylic acid; from about 0.1 to about 5.0 weight percent of glycerin and from about 0.1 to about 5.0 weight percent of protein derived from a collagenous source.

In order to determine whether hair has a normal moisture content, the hair to be tested is dried out in a vacuum oven and accurately weighed. The hair is then allowed to equilibrate at a constant humidity and reweighed accurately. The increased weight is due to moisture pickup. The percent moisture regain is then calculated as follows:

$$\frac{\text{Wt. of hair at a given room humidity} - \text{Wt. of dry hair}}{\text{Wt. of dry hair}} \times 100 = \%$$

The average weight gain for normal hair is approximately 6.3 percent. Moderately moisture deficient hair regains an average of 5.6 percent moisture and severely deficient hair regains an average of 5.0 percent moisture or less.

Depending upon whether the compositions used in the practice of this invention are formulated as shampoos or as various types of conditioners or setting lotions, the compositions used in this invention can include other ingredients which are generally useful for the particular type of compositions. Thus, for example, if the composition is formulated as a shampoo, it can include from about 5 to about 50 weight percent of a suitable detergent such as sodium lauryl sulfate or a sodium lauryl sulfate containing detergent, i.e., Dynol SAM, sold by Richardson Co. alone or together with an amphoteric surface active agent such as the monosodium salt of N-lauryl-iminodipropionic acid, i.e., Deriphat 160C sold by General Mills, which can be present in the shampoo in an amount of from about 0.05 to 10 weight percent, preferably 0.1 to about 5 weight percent of the shampoo, and a nonionic detergent such as a coconut diethanolamide, i.e., Ninol 2012 sold by Stepan Chemical Company. In addition, the shampoo used in the practice of this invention can include foam boosters and stabilizers such as lauryl dimethylamine oxide, i.e., AMMONYX-LO sold by Onyx Chemicals, which can be present in an amount of from about 1 to 15 weight percent, preferably from about 2 to 10 weight percent of the composition. The shampoos can also include chelating agents such as ethylenediaminetetraacetic acid (EDTA), preservatives such as Methyl Parasept sold by Tenneco Chemical Company, glutaraldehyde, monomethyloldimethyl hydantoin and the like. The shampoo formulations can also include perfuming agents, coloring agents and the like.

The conditioning compositions used in the method of this invention can include, in addition to the sodium-2-pyrrolidone-5-carboxylate, glycerin and protein, conditioners such as alkylmethyl bis (polyoxyethylene) quanternary ammonium salt, i.e., Ethoquad 0/12 sold by Armak Chemical Company, which can be present in an amount of from about 0.5 to about 5 weight percent, preferably from about 2 to about 4 weight percent; a cationic surface active agent such as cetyltrimethyl ammonium chloride (29% active) sold under the trademark Barquat CT-429 by Lonza, Inc. and also sold by Armak Chemical Company; stearic acid, which can be present in an amount of from about 0.5 to about 3 weight percent, preferably 1.0 to 2.0 weight percent; glycerol monostearate, which can be present in an amount of from about 0.5 to about 3.0 weight percent, preferably from about 1 to about 2 weight percent; cetyl alcohol which can be present in an amount of about 0.5 to about 5 weight percent, preferably from about 2.0 to about 3 weight percent; polyethylene glycol polymer of ethylene oxide having an average molecular weight of 3,000–3,700 such as that sold by Union Carbide Chemical Company under the tradename Carbowax 4000 which can also be present in an amount of 0.5–5.0 weight percent, and pantothenyl alcohol, which can be present in an amount of 0.05 to 5 weight percent of the composition, in addition to perfuming agents, coloring agents and the like.

It will be understood to those skilled in the art that the above ingredients variously serve as conditioning agents, thickeners and opacifiers, anti-static agents and the like. Generally speaking, when the unique combination of humectants and protein are combined with any or all of the above ingredients, the resulting conditioner is referred to herein as a moisture stabilizing conditioner.

If a moisture control setting conditioner is desired, the three principal ingredients can, for example, be combined with denatured ethanol such as SD alcohol 40, generally at about 25 to 35 weight percent of the composition; from about 1 to about 10 weight percent of a film forming resin such as the 80% vinylpyrrolidone-20% dimethylaminoethyl methacrylate copolymer quaternized with diethyl ammonium sulfate such as GAF Quat 734 sold by General Aniline and Film Corporation; from 0.1 to about 2 weight percent of a quaternary anti-static conditioner such as dimethyl difatty ammonium chloride in aqueous isopropanoc such as that sold by Ashland Chemical Company under the tradename ADOGEN 432 CG, and a cationic surface active agent such as Ethoquad 0/12, identified above. The moisture control setting conditioner can additionally include perfumes and non-ionic surface active agents which also serve as perfume-solubilizers such as a polyoxyalkylene derivative of sorbitan monolaurate, i.e., TWEEN 20 sold by ICI United States, Inc. and coloring agents.

If the hair is to be blown dry or set with hot curlers, a thermal styling protective lotion is provided by combining the protein and two humectants with from about 0.2 to about 10 weight percent, preferably from about 0.5 to about 5 weight percent of, for example, polyvinylpyrrolidone (PVP 30) sold by GAF Corporation, a quaternary conditioner such as a polymer of hydroxyethylcellulose reacted with epichlorohydrin and quaternized with trimethylamine, i.e. Polymer JR 400 sold by Union Carbide Corporation and an anti-static conditioner with 5 percent propylene glycol as a stabilizer such as oleyldimethyl benzyl ammonium chloride, sold under the trademark AMMONYX KP, by Onyx Chemicals. The thermal styling lotion can additionally include perfuming agents and the like.

A moisture conditioner hair spray composition can also be used in the practice of the present invention by incorporating from about 1 to about 15 percent by weight of a water soluble resin consisting of 60% vinylpyrrolidone-40% vinylacetate copolymer, i.e. PVP/VA-E-635, sold by General Aniline and Film Corporation, and from about 0.5 to about 1.5 percent by weight of a copolymer of dimethyl polysiloxane and a polyoxyalkylene ester such as Silicone Fluid SF-1066 sold by General Electric into an alcoholic aqueous solution, containing 40–80 wt. % of SDA 40 alcohol.

The preferred proteins are water or alcohol soluble polypeptides derived from collagenous sources such as those sold under the tradenames Lexoin X250 and WSP-A200 Protein by Inolex Corporation.

The following compositions are illustrative of those which can be used in the practice of this invention.

EXAMPLE 1

MOISTURE STABILIZING SHAMPOO

A moisture stabilizing shampoo composition is formulated using the following ingredients:

| Ingredient | Weight Percent |
| --- | --- |
| Sodium DL-2-pyrrolidone-5-carboxylate (50% aqueous soln.) | 0.10 |
| Glycerin | 0.10 |
| Protein | 0.10 |
| Dynol SAM | 42.00 |
| Ninol 2012 | 1.00 |
| Lauryl dimethylamine oxide | 2.00 |
| Deriphat 160C | 0.10 |
| Water | to 100 percent |

In addition, the above shampoo composition can include preservatives, chelating agents, coloring agents, perfume and the like. The following example illustrates such a composition.

EXAMPLE 2

MOISTURE STABILIZING SHAMPOO

| Ingredient | Weight Percent |
| --- | --- |
| Sodium DL-2-pyrrolidone-5-carboxylate (50% aqueous soln.) | 0.01 |

| Ingredient | Weight Percent |
|---|---|
| Glycerin | 0.10 |
| Protein | 0.10 |
| Dynol SAM | 42.000 |
| Ninol 2012 | 1.000 |
| Lauryl dimethylamine oxide | 2.000 |
| Deriphat 160C | 0.100 |
| Water | to 100 percent |
| Methyl Parasept | 0.150 |
| Versene Flakes | 0.100 |
| Citric acid | 0.190 |
| Monomethylol dimethyl hydantoin | 0.100 |
| Perfume | 0.300 |
| Coloring agent | 0.015 |
| Ammonium chloride | 0.600 |

EXAMPLE 3

MOISTURE STABILIZING CONDITIONER

A moisture stabilizing conditioner is formulated using the following ingredients:

| Ingredient | Weight Percent |
|---|---|
| Sodium DL-2-pyrrolidone-5-carboxylate (50% aqueous soln.) | 0.25 |
| Glycerin | 0.10 |
| Protein | 0.20 |
| Ethoquad 0/12 | 2.50 |
| Carbowax 4000 | 1.50 |
| Stearic acid | 1.50 |
| Glycerol monostearate | 1.50 |
| Cetyl alcohol | 2.50 |
| DL-pantothenyl alcohol | 0.10 |
| Anti-foam agent | 0.20 |
| Preservative | 0.10 |
| Coloring agent | 0.30 |
| Water | to 100 |

EXAMPLE 4

MOISTURE CONTROL SETTING CONDITIONER

A moisture control setting conditioner composition is formulated using the following ingredients:

| Ingredient | Weight Percent |
|---|---|
| Sodium DL-2-pyrrolidone-5-carboxylate (50% aqueous soln.) | 0.500 |
| Glycerin | 1.000 |
| Protein | 1.000 |
| GAF Quat 734 (50% of soln.) | 5.000 |
| Adogen 432 CG | 0.125 |
| Ethoquad 0/12 | 0.375 |
| SD Alcohol | 30.000 |
| Tween 20 | 0.500 |
| Water | to 100 |

The setting conditioner can additionally comprise perfuming agents, coloring agents and the like.

EXAMPLE 5

THERMAL STYLING PROTECTIVE LOTION

A blow-dry conditioning and protective lotion composition is formulated with the following ingredients:

| Ingredient | Weight Percent |
|---|---|
| Sodium-DL-2-pyrrolidone-5-carboxylate | 0.10 |
| Glycerin | 0.10 |
| Lexein X250 | 1.00 |
| PVP 30 | 1.00 |
| Cleyl dimethylbenzyl ammonium chloride | 0.50 |
| Water | to 100.0 |

The blow-dry composition can additionally include perfuming agents, preservatives and the like.

EXAMPLE 6

MOISTURE CONTROL HAIR SPRAY COMPOSITION

A moisture control hair spray composition is formulated from the following ingredients:

| Ingredients | Weight Percent |
|---|---|
| Sodium-DL-2-pyrrolidone-5-carboxylate (50% aqueous soln.) | 0.1 |
| Glycerin | 0.1 |
| Alcohol soluble protein | 0.1 |
| PVP/VA-E-635(50%) | 10.0 |
| Silicone Fluid SF-1066 | 0.2 |
| Citric acid | 0.3 |
| Perfume | 0.3 |
| SDA 40 Alcohol | 78.6 |
| Water | to 100.0 |

In the practice of this invention, hair having a normal moisture content is shampooed, preferably at least once a week, and ideally at least one to three times a week, with a moisture stabilizing shampoo, conditioned by applying a moisture stabilizing conditioner to the freshly shampooed hair, distributing the conditioner throughout the hair and rinsing the conditioner from the hair. If the hair is to be blown dry, a thermal styling protective lotion, such as the lotion of Example 5 is applied to the hair prior to blow drying. If the hair is to be set, for example, on rollers, a moisture control setting conditioner, such as that of Example 4 is distributed throughout the hair prior to setting the hair. If hair spray is used, it is preferred to use the moisture control hair spray composition of Example 6.

It is to be understood that the foregoing examples are intended to be merely illustrative and that modifications and variations will be apparent to those skilled in the art.

I claim:

1. A method for maintaining the normal moisture level of hair comprising the steps of:
   (1) shampooing the hair with a moisture stabilizing shampoo;
   (2) conditioning the shampooed hair with a moisture stabilizing composition;
   (3) thereafter applying a moisture control styling lotion; each of said shampoos, conditioners and lotions comprising from about 0.01 to about 1.0 weight percent of 2-pyrrolidone-5-carboxylate or a salt thereof, from about 0.01 to about 5.0 weight percent of glycerin and from about 0.01 to about 5.0 weight percent of protein derived from a collagenous source.

2. The method of claim 1 wherein the salt of 2-pyrrolidone-5-carboxylate is the sodium salt.

3. The method of claim 1 wherein said styling lotion is a setting conditioner.

4. The method of claim 1 wherein said styling lotion is a thermal styling protective lotion.

5. The method of claim 1 additionally comprising the steps of thereafter styling the hair and applying a moisture control hair spray to the styled hair.

* * * * *